United States Patent
Miyabe

(10) Patent No.: US 8,002,848 B2
(45) Date of Patent: Aug. 23, 2011

(54) TWO-PART HAIR DYE

(75) Inventor: Hajime Miyabe, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/739,631

(22) PCT Filed: Oct. 24, 2008

(86) PCT No.: PCT/JP2008/003034
§ 371 (c)(1),
(2), (4) Date: Apr. 23, 2010

(87) PCT Pub. No.: WO2009/054148
PCT Pub. Date: Apr. 30, 2009

(65) Prior Publication Data
US 2010/0242187 A1    Sep. 30, 2010

(30) Foreign Application Priority Data
Oct. 24, 2007 (JP) ................... 2007-276741

(51) Int. Cl.
*A61Q 5/10* (2006.01)
(52) U.S. Cl. ............ 8/405; 8/431; 8/435; 8/457; 8/477; 8/526
(58) Field of Classification Search ............ 8/405, 431, 8/435, 457, 477, 526
See application file for complete search history.

(56) References Cited

U.S. PATENT DOCUMENTS

| | | | |
|---|---|---|---|
| 2004/0213752 A1* | 10/2004 | Fujinuma et al. | 424/70.1 |
| 2010/0126522 A1 | 5/2010 | Fujinuma et al. | |
| 2010/0126523 A1 | 5/2010 | Fujinuma et al. | |
| 2010/0242187 A1 | 9/2010 | Miyabe | |
| 2010/0316583 A1 | 12/2010 | Fujinuma et al. | |

FOREIGN PATENT DOCUMENTS

| | | |
|---|---|---|
| JP | 11 139945 | 5/1999 |
| JP | 11 199454 | 7/1999 |
| JP | 2003 073240 | 3/2003 |
| JP | 2004 339216 | 12/2004 |
| JP | 2006 124279 | 5/2006 |
| JP | 2007 291015 | 11/2007 |
| JP | 2007 291016 | 11/2007 |
| JP | 2007 314523 | 12/2007 |

OTHER PUBLICATIONS

U.S. Appl. No. 12/739,471, filed Apr. 23, 2010, Miyabe, et al.
U.S. Appl. No. 12/769,182, filed Apr. 28, 2010, Fujinuma, et al.
U.S. Appl. No. 12/739,091, filed Apr. 21, 2010, Fujinuma, et al.
U.S. Appl. No. 12/739,835, filed Apr. 26, 2010, Fujinuma, et al.
U.S. Appl. No. 12/739,610, filed Apr. 23, 2010, Fujinuma, et al.
U.S. Appl. No. 12/995,378, filed Nov. 30, 2010, Ogawa, et al.

* cited by examiner

*Primary Examiner* — Eisa B Elhilo
(74) *Attorney, Agent, or Firm* — Oblon, Spivak, McClelland, Maier & Neustadt, L.L.P.

(57) ABSTRACT

A two-part hair dye including a first part containing an alkali agent, a second part containing hydrogen peroxide, and a non-aerosol foamer vessel to discharge in the form of foam a liquid mixture of the first part and the second part, wherein at least one of the first part and the second part contains a surfactant, 90% by mass or more of the total amount of which being a nonionic surfactant component.

3 Claims, No Drawings

TWO-PART HAIR DYE

FIELD OF THE INVENTION

The present invention relates to a two-part hair dye.

BACKGROUND OF THE INVENTION

Conventionally, hair dye compositions in a form of liquid or cream have been broadly used, however it is not easy to apply them to hair evenly. When a consumer herself applies a dye to her own hair root or the back of her own head, not only skills in a hair blocking or two-mirror technique and the like are required, but also a careful manipulation is required for uniform application.

To simplify the dyeing procedure, it has been proposed to discharge the dye in the form of foam, and two-part aerosol dyes and one-part non-aerosol dyes have been known. Concerning the two-part aerosol dyes, there have been the following problems that: a mixture ratio of the first part and the second part is not constant and uneven bleaching or uneven dyeing is likely to take place; a high pressure metallic vessel may be corroded by oxidation by hydrogen peroxide; and the internal pressure of the high pressure vessel may rise excessively by decomposition of hydrogen peroxide. Concerning the one-part non-aerosol dyes, there have been the following problems that: due to non- or weak bleaching ability, it is difficult to change a color tone substantially with a single dyeing operation; and to dye to a brilliant color tone, it is required to leave the dye on the hair for a long period of time after application or repeat the operation thereby making the dyeing operation rather cumbersome.

On the other hand, two-part hair dye compositions to be discharged in the form of foam from a non-aerosol foamer vessel have been proposed (Patent Document 1 and Patent Document 2). By discharging a liquid mixture of the first and second parts from the non-aerosol foamer vessel in the form of foam, the mixture ratio thereof can be more constant than the conventional two-part aerosol dyes, and sufficient bleaching ability and dyeability compared with the conventional one-part non-aerosol dyes can be obtained.
Patent Document 1: JP-A-2004-339216
Patent Document 2: JP-A-2006-124279

SUMMARY OF THE INVENTION

The present invention provides a two-part hair dye including a first part containing an alkali agent, a second part containing hydrogen peroxide, and a non-aerosol foamer vessel to discharge in the form of foam a liquid mixture of the first part and the second part, wherein at least one of the first part and the second part contains a surfactant, 90% by mass or more of the total amount of which being a nonionic surfactant component.

The present invention further provides a method for dyeing head hair, including the steps of discharging in the form of foam the aforedescribed liquid mixture in the two-part hair dye from a non-aerosol foamer vessel; applying the foam to the head hair; and re-foaming the foam on the head hair.

DETAILED DESCRIPTION OF THE INVENTION

The present invention relates to a two-part hair dye in the form of foam superior in preservation stability, ease of application to the head hair and low irritation to the scalp while maintaining the advantages of good bleaching ability and dyeability according to Patent Document 1 and Patent Document 2.

The present inventors have discovered that the aforedescribed object can be attained by making the proportion of a nonionic surfactant to 90% by mass or more of the total amount of surfactant contained in the liquid mixture of the first and second parts of the non-aerosol two-part hair dye.

According to the present invention, the liquid mixture of the first and second parts can be discharged in the form of foam and applied to the head hair evenly and easily. The discharged foam of the liquid mixture is compatible to the head hair, so that a large amount can be applied; is free from irritation to the scalp, splashing of the liquid, or dripping of the liquid; and has sufficient bleaching ability or dyeability. Consequently, the hair dye of the present invention can realize easily and comfortably a uniform and less uneven bleaching or dyeing.

The liquid mixture discharged in the form of foam by gas/liquid mixing using the non-aerosol foamer vessel can reach easily the hair root without forming a liquid pool spreading appropriately over a part of the head hair to be bleached or dyed. Consequently, extreme blonding at the hair root or uneven bleaching or dyeing caused by unevenness in the coated amount of the liquid mixture does not occur as in the case of a conventional liquid or cream dye. Therefore the hair dye of the present invention can be applied to the head hair at new growth areas near a part or a face line, so that color difference between the new growth area and previously dyed area can be eliminated to achieve a natural finish. Further, since the liquid mixture can be applied to the head hair in an appropriate amount, damages to the head hair can be reduced.

The surfactant can be contained in one or both of the first part containing an alkali agent, and the second part containing hydrogen peroxide. In any case, if the proportion of the nonionic surfactant in the total amount of surfactant is 90% by mass or higher, the preservation stability is good, and the discharged foam of the liquid mixture can be kept in good foam quality stably over time.

DEFINITIONS

A head hair means herein a hair fixed on the head, and a hair separated from the head, such as a wig or a tress, is excluded. Although there is no restriction on a head hair, from a doll's hair to an animal hair, a human hair is preferable.

Herein a simple expression of a "two-part dye" refers to a broad concept including also a non-aerosol foamer vessel. Further, the two-part dye refers to a concept including both a hair dye containing a dyestuff, and a bleach not containing a dyestuff. Furthermore, a "liquid mixture in the two-part dye" means the liquid mixture of the first and second parts. A method for dyeing the head hair refers to a concept including a method for bleaching the head hair.

[Alkali Agent]

As the alkali agent to be contained in the first part, for example, ammonia, an alkanolamine such as ethanolamine, sodium hydroxide and potassium hydroxide can be used. Further, as a buffer, an ammonium salt, such as ammonium hydrogencarbonate and ammonium chloride, and a carbonate, such as potassium carbonate and sodium hydrogen carbonate may be appropriately added.

The pH of the liquid mixture of the first and second parts of the two-part hair dye of the present invention is preferably 8 to 11, more preferably 9 to 11, and the amount of the alkali agent for use is adjusted appropriately so that the pH of the liquid mixture fall within the above range.

[Hydrogen Peroxide]

The hydrogen peroxide content in the second part is preferably 1 to 9% by mass and more preferably 3 to 6% by mass, and the hydrogen peroxide content in the liquid mixture of the first and second parts is preferably 1 to 6% by mass and more preferably 2 to 5% by mass. While, the pH of the second part is preferably 2 to 6 and more preferably 2.5 to 4, in order to prevent decomposition of the hydrogen peroxide.

[Surfactant]

A surfactant is added to one or both of the first part and the second part, so that stable foam is easily generated by mixing the liquid mixture in the two-part hair dye with air by a foam discharge means of the foamer vessel. According to the present invention, the proportion of the nonionic surfactant in the total amount of surfactant is made to 90% by mass or more, to generate the foam easily applicable and compatible to the head hair. The proportion of the nonionic surfactant in the total amount of surfactant is preferably 95% by mass or higher, and more preferably 98% by mass or higher. The total amount of the surfactant in the liquid mixture of the first and second parts is preferably 0.1 to 30% by mass, more preferably 0.5 to 20% by mass, and even more preferably 1 to 15% by mass.

(Nonionic Surfactant)

As a nonionic surfactant, nonionic surfactants of a polyoxyalkylene addition type, a sugar type, a glycerin type and an alkanolamide type are exemplified. The polyoxyalkylene addition type includes an ether type such as a polyoxyethylene alkyl ether, and an ester type such as a polyoxyethylene fatty acid ester; the sugar type includes a sugar ether type such as an alkyl polyglucoside, a sugar ester type such as a sucrose fatty acid ester or a sorbitan fatty acid ester, and a sugar amide type such as a fatty acid glycolamide; the glycerin type includes an alkyl glyceryl ether, a glycerin fatty acid ester; and the alkanolamide type includes a fatty acid mono-alkanolamide, a fatty acid diethanolamide.

Thereby the polyoxyethylene alkyl ether type nonionic surfactant has preferably a $C_{10}$ to $C_{20}$, more preferably $C_{12}$ to $C_{18}$ alkyl group, which is preferably linear. The average mole number of added polyoxyethylene groups is preferably 1 to 40, and more preferably 4 to 30. As the polyoxyethylene fatty acid ester type nonionic surfactant are preferable a polyoxyethylene hydrogenated castor oil, a polyoxyethylene glycerin fatty acid ester, and those having a fatty acid residue with $C_{10}$ to $C_{20}$ and more preferably $C_{12}$ to $C_{18}$, which is preferably a linear alkyl group. The alkyl polyglucoside type nonionic surfactant has preferably a $C_8$ to $C_{18}$, more preferably $C_8$ to $C_{14}$, even more preferably $C_9$ to $C_{11}$ alkyl group, which is preferably linear. The average polymerization degree of the glucoside is preferably 1 to 5, and more preferably 1 to 2. As the sucrose fatty acid ester type nonionic surfactant, a glycol mono-fatty acid ester and a glycol di-fatty acid ester, and that with a fatty acid residue having $C_{12}$ to $C_{22}$ is preferable. For the alkyl glyceryl ether type nonionic surfactant, the alkyl group is preferably with $C_8$ to $C_{22}$, and more preferably $C_{12}$ to $C_{18}$. Further, the average mole number of the added glycerin is preferably 1 to 4, and more preferably 1 to 2. The glycerin fatty acid ester type nonionic surfactant has preferably a fatty acid residue with $C_{10}$ to $C_{20}$, and more preferably $C_{12}$ to $C_{18}$, which is preferably a linear alkyl group. Further, the average mole number of the added glycerin is preferably 1 to 10, and more preferably 1 to 4. As the fatty acid mono-alkanolamide or fatty acid diethanolamide type nonionic surfactant, that having a fatty acid residue with $C_{12}$ to $C_{22}$ is preferable.

Among them, the polyoxyethylene alkyl ether type nonionic surfactant and the alkyl polyglucoside type nonionic surfactant are preferable in view of the foaming property and the stability.

Two or more of the nonionic surfactants may be used together.

(Other Surfactants)

Although a surfactant other than the nonionic surfactant may be used together, the content of the surfactant other than the nonionic surfactant should not exceed 10% by mass of the total amount of the surfactants in the liquid mixture of the first and second parts. Examples of such other surfactants include an anionic surfactant, an amphoteric surfactant, a semipolar surfactant, and a cationic surfactant.

Examples of the anionic surfactant include a sulfate ester surfactant, such as an alkyl sulfate and an alkyl ether sulfate; a sulfonate surfactant, such as a sulfosuccinate salt, an isethionate salt, a taurine salt, an alkylbenzene sulfonic acid, an α-olefin sulfonic acid, and an alkane sulfonic acid; and a carboxylate surfactant, such as a fatty acid salt, an N-acylamino acid salt (e.g. N-acylsarcosine salt, N-acylglutamic acid salt and N-acylglycin salt), a salt of an alkylsuccinate or alkenylsuccinate, an alkyl ether carboxylate salt, and a fatty acid amide ether acetate salt.

Examples of the amphoteric surfactant include surfactants of a carbobetaine type, an amidobetaine type, a sulfobetaine type, a hydroxysulfobetaine type, an amidosulfobetaine type, a phosphobetaine type and an imidazolinium type, having a $C_8$ to $C_{24}$ alkyl, alkenyl or acyl group.

Examples of the semipolar surfactant include an alkylamine oxide.

Examples of the cationic surfactant include cationic surfactants of a tertiary amine salt type and a quaternary ammonium salt type, having a $C_8$ to $C_{24}$ alkyl, alkenyl or acyl group.

Two or more of such other surfactants may be used together.

[Higher Alcohol]

The two-part hair dye of the present invention may contain additionally a higher alcohol in order to improve the foam stability so that the two-part hair dye of the present invention should not drip after application to the head hair during being left thereon.

The higher alcohol has preferably a $C_{10}$ to $C_{30}$, more preferably $C_{12}$ to $C_{24}$, even more preferably $C_{14}$ to $C_{22}$ alkyl or alkenyl group, more preferably the alkyl group, and even more preferably the linear alkyl group. Examples thereof include myristyl alcohol, cetanol, stearyl alcohol, arachyl alcohol, behenyl alcohol, and oleyl alcohol.

Two or more of the higher alcohols may be used together, and added in either or both of the first part and the second part. The content of the higher alcohol in the liquid mixture of the first and second parts is preferably 0.01 to 1% by mass, more preferably 0.1 to 0.8% by mass, even more preferably 0.2 to 0.7% by mass and even more preferably 0.3 to 0.6% by mass so that the foaming becomes easy, the foam becomes soft and smooth, and dripping during being left on the head hair can be efficiently prevented. If the higher alcohol is added to the first part, the content therein is preferably 0.01 to 2% by mass, more preferably 0.1 to 1.5% by mass, and even more preferably 0.2 to 1% by mass. If the higher alcohol is added to the second part, the content therein is preferably 0.01 to 2% by mass, more preferably 0.1 to 1.5% by mass and even more preferably 0.5 to 1% by mass.

[Nonvolatile Hydrophilic Solvent]

Preferably either of the first part and the second part contains also a nonvolatile hydrophilic solvent. Owing thereto, the irritation to the scalp caused by the concentration of irritating components such as hydrogen peroxide due to the evaporation of water from the hair dye, while the applied two-part hair dye of the present invention is left on the head hair, can be mitigated. As the nonvolatile hydrophilic solvent, polyols and lower alkyl ($C_1$ to $C_4$) ethers thereof not having anti-foaming activity are preferable. For polyols, those with $C_2$ to $C_6$ are preferable. Examples thereof include glycerin, propylene glycol, dipropylene glycol, 1,3-butanediol, ethylene glycol, diethylene glycol, isoprene glycol, and sorbitol. Examples of the lower alkyl ethers of the polyols include a mono-lower alkyl ether and a poly-lower alkyl ether (e.g. di-lower alkyl ether) of the polyol. Among others, a monomethyl ether or a monoethyl ether of the polyol is preferable. Specific examples thereof include ethylene glycol monomethyl ether, ethylene glycol monoethyl ether, diethylene glycol monomethyl ether and diethylene glycol monoethyl ether. Two or more thereof may be used together.

The content of the nonvolatile hydrophilic solvent in the liquid mixture of the first and second parts is preferably 0.01 to 4% by mass, more preferably 0.1 to 3% by mass, and even more preferably 0.2 to 2% by mass in order to decrease the irritation to the scalp and to obtain the quality foam at a lower temperature.

[Dye]

The two-part hair dye of the present invention can be used for bleaching the head hair, when the liquid mixture of the first and second parts does not contain a dye, and used for dyeing the head hair, when the liquid mixture contains an oxidation dye or a direct dye. For dying purpose, the first part contains the oxidation dye or the direct dye. Examples of the oxidation dye include a dye precursor, such as p-phenylenediamine, p-aminophenol, toluene-2,5-diamine, N,N-bis(2-hydroxyethyl)-p-phenylenediamine, 2-(2-hydroxyethyl)-p-phenylenediamine, 4-amino-3-methylphenol, 6-amino-3-methylphenol, o-aminophenol, and 1-hydroxyethyl-4,5-diaminopyrazole; and a coupler, such as resorcinol, 2-methylresorcinol, m-aminophenol, p-amino-o-cresol, 5-(2-hydroxyethylamino)-2-methylphenol, m-phenylenediamine, 2,4-diaminophenoxyethanol, and 1-naphthol. Examples of the direct dye include p-nitro-o-phenylenediamine, p-nitro-m-phenylenediamine, Basic Yellow 87, Basic Orange 31, Basic Red 12, Basic Red 51, Basic Blue 99.

[Silicones]

In order to keep the discharged foam stable for a long time, it is desirable that the two-part hair dye of the present invention does not contain a silicone in the liquid mixture of the first and second parts. However, to make the foam smooth and compatible to the head hair and to impart a high conditioning effect to the head hair, the liquid mixture may contain also a silicone within a certain range. Examples of the silicones include dimethylpolysiloxane, methylphenylpolysiloxane, polyether modified silicone, amino modified silicone, oxazoline modified silicone elastomer and emulsions dispersing the same in water using a surfactant. Among them, polyether modified silicone, amino modified silicone, and the emulsions thereof are preferable, because they can be dispersed in water stably without using a thickener.

Polyether modified silicone includes an end-modified type and a side chain-modified type, such as a pendant (pectinate) type, a both end-modified type, a one end-modified type. Examples of the modified silicone include a dimethylsiloxane/methyl(polyoxyethylene)siloxane copolymer, a dimethylsiloxane/methyl(polyoxypropylene)siloxane copolymer, and a dimethylsiloxane/methyl(polyoxyethylene-polyoxypropylene)siloxane copolymer. The HLB of the polyether modified silicone is preferably 10 or higher, more preferably 10 to 18, in view of compatibility with water. Thereby the HLB values are to be determined by the phenol index (the phenol index is an index correlated with HLB, applicable to an ether type nonionic surfactant).

Although the amino modified silicone having an amino group or an ammonium group is usable, amodimethicone is preferred.

If the silicone is added in the liquid mixture of the first and second parts, the content thereof is preferably 2% by mass or less, more preferably 0.005 to 1% by mass, and even more preferably 0.01 to 0.5% by mass in order not to interfere with foaming, and to make the foam smooth and compatible to the head hair, and to impart a high conditioning effect to the head hair.

[Other Components]

The first part and the second part may contain as necessary a perfume, a UV absorber, a metal chelating agent such as edetic acid, an antibacterial agent, an antiseptic agent such as methyl-p-hydroxybenzoate, a stabilizer, such as phenacetin, etidronic acid, or oxyquinoline sulfate, an organic solvent, such as ethanol, benzyl alcohol, or benzyloxy ethanol, a water-soluble polymer such as hydroxyethyl cellulose, and a humectant. The liquid mixture of the first and second parts contains preferably a medium composed mainly of water.

Further, a persulfate such as ammonium persulfate may be added in the liquid mixture as the third part in order to improve the bleaching activity.

[Viscosity]

The viscosity (25° C.) of the first part is preferably 1 to 50 mPa·s, more preferably 3 to 40 mPa·s, and even more preferably 5 to 30 mPa·s. The viscosity (25° C.) of the second part is preferably 1 to 300 mPa·s, more preferably 3 to 200 mPa·s, and even more preferably 5 to 100 mPa·s. The viscosity (25° C.) of the liquid mixture of the first and second parts is preferably 1 to 300 mPa·s, more preferably 1 to 100 mPa·s, even more preferably 3 to 100 mPa·s, even more preferably 3 to 80 mPa·s, even more preferably 3 to 50 mPa·s, even more preferably 5 to 50 mPa·s, even more preferably 5 to 30 mPa·s, and even more preferably 10 to 30 mPa·s. The viscosity is measured by a B-type rotational viscometer (Model TV-10 from Tokimec Inc.) using a rotor No. 1 which is rotated for 1 min. before the measurement. If the viscosities of subjects to be measured are 100 mPa·s or below, between 100 and 200 mPa·s or between 200 and 500 mPa·s, the measurement is conducted at the rotation speeds of 60 rpm, 30 rpm, and 12 rpm, respectively. By adjusting the viscosity of the liquid mixture in the above range, the liquid mixture can be mixed uniformly without foaming, which can form uniform foams easily applicable to the head hair, compatible to the head hair, and resistant to drip after the application.

By adjusting the viscosity in the above range, the foam easily applicable and compatible to the head hair and resistant to drip after the application to the head hair can be obtained, and discharge of the foam from the non-aerosol foamer vessel becomes easy. For adjusting the viscosity within such range, a water-soluble solvent such as ethanol is added, or the contents and types of a surfactant, a polyol, or a higher alcohol should be appropriately adjusted.

[Air/Liquid Mixing Ratio]

The air/liquid mixing ratio (air/the liquid mixture) of the foam discharged from the foamer vessel is preferably 10 to 50 mL/g, more preferably 15 to 40 mL/g, and even more preferably 20 to 30 mL/g in view of compatibility and easy applicability of the foam to the head hair. Thereby the air/liquid mixing ratio is measured as follows.

The air/liquid mixing ratio is determined by measuring the mass and the volume of the foam discharged at 25° C. In the foamer vessel 100 g of the liquid mixture is poured and 20 g of foam is discharged into a 1,000 mL-measuring cylinder and the volume thereof is measured 1 min. after the start of discharging. The discharged foam volume (mL) is divided by the mass of 20 g to give the air/liquid mixing ratio (mL/g).
[Foamer Vessel]

The foamer vessel of the present invention is a non-aerosol vessel that discharges the first and second parts in the form of foam by mixing them with air without using a propellant. Moreover, with the use of the foamer vessel, spattering of the discharged dye can be prevented. A non-aerosol vessel can be produced at a lower cost compared with an aerosol vessel, can be regulated easily for the discharging speed, is recyclable with certain treatment, and can be handled safely during the product distribution because a high pressure propellant gas is not involved.

As the foamer vessel, any non-aerosol vessel with a foam discharging means, such as a pump foamer vessel and a squeeze foamer vessel publicly known and having a foam discharging means, can be used.

The pump foamer or squeeze foamer vessel has a foam generating part such as a net, whose thickness is preferably thin so that clogging caused by the dried-up liquid mixture of the first and second parts can be immediately removed at the next discharge by the foam flow dissolving the clogged sold. Thereby the mesh size of the net is preferably 50 to 280 mesh, more preferably 90 to 250 mesh, and even more preferably 130 to 220 mesh. By use of the net with such mesh size, creamy foam can be generated. Preferable examples of a material for the net include nylon, polyethylene, polypropylene, polyester, Teflon (registered trade name), carbon fibers, and stainless steel. More preferable are nylon, polyethylene, polypropylene, and polyester, and even more preferable is nylon.

The foamer vessel to be used for the two-part hair dye of the present invention is provided with at least one of, preferably plural of, and more preferably 2 of such net in view of economy and stability of the foam. Thereby the mesh size of the net that the liquid first passes is coarser than or same as the net passed next.

A part of the foamer vessel that contacts the content (e.g. the inner wall of the vessel, the inner wall of the foaming discharging device) is preferably composed of a material that is not corroded by alkali or hydrogen peroxide, and is permeable to oxygen generated by decomposition of the hydrogen peroxide.

As a product form of the two-part hair dye of the present invention composed of the first part, the second part and the foamer vessel, the first part and the second part may be filled in respective vessels separated from the foamer vessel and they are transferred to the foamer vessel before use to be mixed, or either part may be filled in the foamer vessel, while the other part is packaged in a separate vessel, which is transferred to the foamer vessel before use. Thereby the second part is preferably filled in the foamer vessel constituted of a vessel with gas permeability so that the increase of the vessel inner pressure by the oxygen generated by the decomposition of the hydrogen peroxide can be prevented, more preferably filled in the foamer vessel constituted with a material having oxygen permeability (e.g. polypropylene and polyethylene). In contrast, for the first part an oxygen non-permeable vessel should be used to prevent oxidation of the oxidation dye.
[Method for Dyeing Head Hair]

In the method for dyeing the head hair according to the present invention, the head hair should preferably be combed in advance of application of the discharged foam, which suppresses the head hair to tangle during a re-foaming treatment and prevents the hair dye from spattering. Further, after combing the head hair, the blocking procedure as commonly conducted is not required, and the omission of the blocking procedure is preferable. This makes the step of applying the hair dye to the head hair and the step of refoaming described below easier.

The head hair to be treated by the hair dye should preferably have not been treated with a hair dressing immediately before the dyeing treatment so that dripping is prevented, uniform dyeing and a sufficient dyeing effect can be obtained. Further the head hair should be preferably dry so that the liquid mixture is not diluted, dripping is prevented, and uniform dyeing and a sufficient dyeing effect can be obtained. If the head hair is shampooed immediately before the hair dyeing treatment, the head hair should be preferably dried before the dyeing treatment. Thereby drying the head hair means to remove a liquid composed mainly of water attached to the head hair by reason of the shampooing, to the extent that the liquid does not spontaneously drip. Specifically, towel-drying or blow-drying is preferable.

The liquid mixture of the first and second parts discharged in the form of foam is, after once receiving the same by hand or a brush, or directly, applied to the head hair. If it is received by hand, it is preferable to wear gloves. Since by the method for dyeing the head hair according to the present invention, the blocking procedure as commonly conducted in applying the hair dye can be omitted, the foam can be applied quickly. Consequently, application can start at an arbitrary location of the head hair, differently from the rule for a conventional liquid or creamy two-part hair dye, that the application need not start from the hair at the neckline. The application may start at a location of interest, and preferably start at the hairline or the part.

It is preferable to discharge the foam approximately to a lemon size, because the size is appropriate to receive by one hand and to apply the same to the head hair by the hand. In this case, the procedure to discharge the foam is conducted by a hand, which is received by the other hand. After the once received foam is applied to the head hair, the procedures of the discharge of the foam to the hand and the application thereof to the head hair are repeated. This series of the procedures can be carried out very easily and quickly.

The applied range of the foam may be the entirety of the head hair or only a specific part thereof.

Next, the applied foam is re-foamed on the head hair. This re-foaming may be conducted by gas injection, by use of an instrument, such as a vibrator or a brush, or by fingers, however use of fingers is preferable, because thereby the two-part hair dye can be spread also to the hair root adequately. The re-foaming speed with the vibrator, the brush or the fingers should be preferably so regulated, that the foam does not spatter around.

Thereby the re-foaming may be conducted after the foam has completely disappeared, or during the foam is disappearing, or before the applied foam starts to change. Further, it may be conducted after the foam is applied to all the intended area, or halfway in the application. The re-foaming may be conducted once continuously, or intermittently repeated more than once. Thereby continuous re-foaming means the vibrator, the brush or the fingers used for re-foaming continue to touch a part of the head hair, or retouch the same within 1 sec., even if the contact is lost once. In short, observing the applied region, the foam should be re-foamed appropriately at latest before the dripping of a liquid from the applied foam should take place. By re-foaming the disappearing foam, the dripping can be prevented irrespective of the nature of the foam.

Furthermore, despite of a difference in the nature of a foam caused by a difference in a structure of the foamer vessel or the composition of the two-part hair dye, the nature of the foam can be modified to that suitable for hair dyeing by the re-foaming. Although it may be possible to obtain the foam maintaining stably the quality suitable for hair dyeing without dripping by selecting specifically a structure of the foamer vessel and the composition of the two-part hair dye, it is still desirable in such a case to re-foam at least once as soon as possible after the completion of the application of the form. The re-foaming at an earlier stage can prevent unevenness in color over the region to be applied. The timing thereof is preferably within 5 min. after the completion of the application of the discharged foam to the head hair, more preferably within 3 min., and even more preferably within 1 min.

Specific examples of the preferable stepwise procedure of discharging the foam, applying the same to the head hair, and re-foaming will be described separately for partial dyeing and whole head dyeing.

[Partial Dyeing]

1) An appropriate amount of the foam is discharged onto a hand, which is applied to a part of the head hair and re-foamed once for 1 sec. to 10 min., preferably for 3 sec. to 3 min.

2) An appropriate amount of the foam is discharged onto a hand, which is applied to a part of the head hair and re-foamed 2 to 30 times, each time for 1 sec. to 10 min., preferably for 3 sec. to 3 min., totaling spending 2 sec. to 20 min., and preferably 5 sec. to 5 min.

[Whole Head Dyeing]

3) An appropriate amount of the foam is discharged onto a hand, which is applied to a part of the head hair and re-foamed once for 3 sec. to 10 min., preferably for 5 sec. to 3 min. The procedure is repeated to apply the foam to the whole head.

4) An appropriate amount of the foam is discharged onto a hand, which is applied to a part of the head hair and re-foamed once for 3 sec. to 10 min., preferably for 5 sec. to 3 min. The procedure is repeated to apply the foam to the whole head, and then re-foamed once for 3 sec. to 10 min., preferably for 5 sec. to 3 min. Further, an appropriate amount of the foam is discharged onto a hand, which is applied to a part of the head hair additionally and re-foamed over the whole head once for 3 sec. to 10 min., preferably for 5 sec. to 3 min.

5) An appropriate amount of the foam is discharged onto a hand, which is applied to a part of the head hair and re-foamed once for 3 sec. to 10 min., preferably for 5 sec. to 3 min. The procedure is repeated to apply the foam to the whole head. After the completion of the application to the whole head, the re-foaming is conducted once for 3 sec. to 10 min., preferably 5 sec. to 5 min.

6) An appropriate amount of the foam is discharged onto a hand, which is applied to a part of the head hair and re-foamed once for 3 sec. to 10 min., preferably for 5 sec. to 3 min. The procedure is repeated to apply the foam to the whole head. After the completion of the application to the whole head, the re-foaming over the whole head is conducted 2 to 30 times each time for 3 sec. to 10 min., preferably 5 sec. to 3 min., totaling spending 6 sec. to 20 min., preferably 10 sec. to 5 min.

7) An appropriate amount of the foam is discharged onto a brush, which is applied to a part of the head hair. The procedure is repeated to apply the foam to the whole head and re-foamed with the same brush over the whole head for 3 sec. to 10 min., preferably for 5 sec. to 5 min.

8) An appropriate amount of the foam is discharged onto a brush, which is applied to a part of the head hair and re-foamed once with the same brush or by hand over 3 sec. to 10 min., preferably for 5 sec. to 3 min. The procedure is repeated to apply the foam to the whole head. After the completion of the application to the whole head, the re-foaming is conducted once with the same brush or by hand for 3 sec. to 10 min., preferably 5 sec. to 5 min.

The re-foaming may be conducted over the whole hair or over a limited region. If the re-foaming is conducted over the whole hair, even when the foam be failed to be applied to an unseeable part such as the hair at the back of the head, the foam can be distributed totally and an undyed area can be eliminated. If the re-foaming is carried out at a certain limited area by a partial dyeing, the border of the dyed area can be gradated to give a natural finish. Furthermore, after re-foaming the distribution of the foam becomes easily seeable, and existence of an undyed part in the area to be dyed can be avoided.

The foam is washed off about 3 to 60 min., preferably about 5 to 45 min. after the completion of the application thereof. Thereby the time after the completion of the application of the form is the total required time from the completion of the application of the foam to the whole head or the intended area, until the washing, namely a concept including the time for being left on the head hair as well as the time required for re-foaming. Thereafter the head hair is appropriately shampooed, rinsed, washed with water and dried.

EXAMPLES

Examples 1 to 3 and Comparative Example 1

The first part and the second part of each two-part hair dye according to the compositions listed in Table 1 were prepared, and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed.

Comparative evaluations between the two-part hair dyes in the form of foam of Examples 1 to 3, and Comparative Example 1 on "applicability of the foam" and "compatibility of the foam" were carried out by 10 test subjects as follows: To the wig of the same hairstyle with the hair cut on the chin line (Beaulax Co., Ltd., No. 775S), the subjects were asked to carry out the following application procedure starting from the dry state of the head hair, with the respective two-part hair dyes in the form of foam.

1. To the vessel of the squeeze foamer containing 60 g of the second part, 40 g of the first part was added, and the liquid mixture of the first and second parts is mixed avoiding foaming and the squeeze foamer is mounted.

2. After wearing gloves, the squeeze vessel standing upright is squeezed by one hand to discharge the liquid mixture in the form of foam onto the palm of the other hand.

3. The liquid mixture in the form of foam is applied to the dry head hair.

4. Repeating the steps 2 and 3, 80 g of the liquid mixture is applied to the whole hair.

5. The applied liquid mixture is re-foamed by massaging the whole hair with fingers for 15 sec.

6. Leave it for 10 min.

7. The applied liquid mixture is re-foamed by massaging the whole hair with fingers for 25 sec.

8. After the completion of the re-foaming according to the step 7, leave it for 20 min.

9. The whole hair is washed with warm water, followed by shampooing, rinsing and drying successively.

The rating points are defined as below relative to Comparative Example 1 as the bench mark (containing Na laureth sulfate as an anionic surfactant, as in the example of Patent Document 1), and the sums of the rated points are shown also in Table 1.

[Rating Points]

"Applicability of Foam"

Substantially better applicability than Comparative Example 1: +2 point

Better applicability than Comparative Example 1: +1 point

Equivalent applicability to Comparative Example 1: 0 point

Poorer applicability than Comparative Example 1: −1 point

Substantially poorer applicability than Comparative Example 1: −2 point

"Compatibility of Foam"

Substantially better compatibility than Comparative Example 1: +2 point

Better compatibility than Comparative Example 1: +1 point

Equivalent compatibility to Comparative Example 1: 0 point

Poorer compatibility than Comparative Example 1: −1 point

Substantially poorer compatibility than Comparative Example 1: −2 point

Furthermore, each mixture of the first part and the second part at the ratio by mass of 1:1.5 was applied to each goat hair tress (10 cm, about 1 g, from Beaulax Co., Ltd.) at the bath ratio of 1:1, left thereon for 30 min., and then washed with water and shampooed. After drying, the color of the tress was measured by a colorimeter (CR400 from Konica Minolta Sensing Inc.) and the "dyeability" was evaluated by the color difference (ΔE) from that of the goat hair tress before dyeing. The average value of the evaluation results (N=3) was used for comparison.

TABLE 1

|  | Ex. 1 | Ex. 2 | Ex. 3 | Com. Ex. 1 |
|---|---|---|---|---|
| First part (% by mass) | | | | |
| p-Aminophenol | 0.3 | 0.3 | 0.3 | 0.3 |
| m-Aminophenol | 0.1 | 0.1 | 0.1 | 0.1 |
| p-Amino-o-cresol | 0.3 | 0.3 | 0.3 | 0.3 |
| Toluene-2,5-diamine | 0.9 | 0.9 | 0.9 | 0.9 |
| Resorcinol | 0.8 | 0.8 | 0.8 | 0.8 |
| Aqueous ammonia (28% by mass) | 3.0 | 3.0 | 3.0 | 3.0 |
| Ethanolamine | 1.0 | 1.0 | 1.0 | 1.0 |
| Ammonium hydrogencarbonate | 2.5 | 2.5 | 2.5 | 2.5 |
| Decyl glucoside | 5.0 | — | — | — |
| Lauryl glucoside | — | 5.0 | — | — |
| Laureth-23 | — | — | 5.0 | — |
| Sodium laureth sulfate | — | — | — | 5.0 |
| Ethanol | 10.0 | 10.0 | 10.0 | 10.0 |
| Propylene glycol | 4.0 | 4.0 | 4.0 | 4.0 |
| EDTA-4Na | 0.1 | 0.1 | 0.1 | 0.1 |
| Ascorbic acid | 0.4 | 0.4 | 0.4 | 0.4 |
| Anhydrous sodium sulfite | 0.5 | 0.5 | 0.5 | 0.5 |
| Perfume | 0.5 | 0.5 | 0.5 | 0.5 |
| Water | Balance | Balance | Balance | Balance |

TABLE 1-continued

|  | Ex. 1 | Ex. 2 | Ex. 3 | Com. Ex. 1 |
|---|---|---|---|---|
| Second part (% by mass) | | | | |
| Aqueous hydrogen peroxide solution (35% by mass) | 16.3 | 16.3 | 16.3 | 16.3 |
| Decyl glucoside | 5.0 | — | — | — |
| Lauryl glucoside | — | 5.0 | — | — |
| Laureth-23 | — | — | 5.0 | 5.0 |
| Cetanol | 0.6 | 0.6 | 0.6 | 0.6 |
| Etidronic acid | 0.08 | 0.08 | 0.08 | 0.08 |
| Aqueous sodium hydroxide solution (48% by mass) | * | * | * | * |
| Water | Balance | Balance | Balance | Balance |
| Applicability of foam | +10 | +10 | +9 | Bench mark |
| Compatibility of foam | +10 | +10 | +9 | Bench mark |

*: Amount required to adjust the pH of the second part to 3.5

Since in Examples 1 to 3, each bubble composing the foam was small in size and the foam was stable compared with that in Comparative Example 1 when discharged onto the hand palm, as shown in Table 1, the foam was easy to apply to the head hair, spread well over the head hair and was resistant to drip, in short, it was compatible to the head hair. Furthermore, ΔE was in all of Examples 1 to 3 and Comparative Example 1 within the range of 61±1, indicating the equivalent dyeability.

Example 4

| | (% by mass) |
|---|---|
| (First part) | |
| Aqueous ammonia (28% by mass) | 3.0 |
| Ethanolamine | 1.5 |
| Ammonium hydrogencarbonate | 0.3 |
| Decyl glucoside | 8.0 |
| Laureth-20 | 2.0 |
| Myristyl alcohol | 0.3 |
| Propylene glycol | 4.0 |
| Ethanol | 9.5 |
| Perfume | 0.5 |
| Purified water | balance |
| (Second part) | |
| Aqueous hydrogen peroxide solution (35% by mass) | 16.3 |
| Decyl glucoside | 0.5 |
| Cetanol | 0.4 |
| Etidronic acid | 0.1 |
| Aqueous sodium hydroxide solution (48% by mass) | Amount required to adjust pH to 3.5 |
| Purified water | balance |

The semi-long hair of the 20s-age female test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the head hair, which was repeated until 80 g was applied all over the head hair previously dried. After completion of the application, the re-foaming was carried out with fingers for 20 sec., then the foam was left on the head hair at room temperature for 30 min., then the head hair was washed, shampooed, rinsed and dried.

Thereby the discharged foam was uniform and fine, was smoothly applicable and compatible to the head hair without dripping. The applied foam gave substantially no irritating feeling to the scalp while being left on the head hair, and no bleaching unevenness. The whole hair was almost uniformly bleached.

Example 5

|  | (% by mass) |
| --- | --- |
| (First part) | |
| Aqueous ammonia (28% by mass) | 3.0 |
| Ethanolamine | 1.5 |
| Ammonium hydrogencarbonate | 0.3 |
| p-Phenylenediamine | 0.1 |
| p-Aminophenol | 0.2 |
| p-Amino-o-cresol | 0.4 |
| Decyl glucoside | 8.0 |
| Laureth-23 | 2.0 |
| Myristyl alcohol | 0.2 |
| Propylene glycol | 4.0 |
| Ethanol | 9.5 |
| Perfume | 0.5 |
| Purified water | balance |
| (Second part) | |
| Aqueous hydrogen peroxide solution (35% by mass) | 16.3 |
| Lauryl glucoside | 0.5 |
| Potassium laurate | 0.1 |
| Etidronic acid | 0.1 |
| Aqueous sodium hydroxide solution (48% by mass) | Amount required to adjust pH to 3.5 |
| Purified water | balance |

The semi-long hair of the 20s-age female test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the head hair and re-foamed at the applied region for 2 sec. with fingers, which procedure was repeated until 80 g was applied all over the head hair previously dried. After completion of the application, the re-foaming was carried out with fingers for 20 sec., then the foam was left on the head hair at room temperature for 25 min., then the head hair was washed, shampooed, rinsed and dried.

Thereby the discharged foam was uniform and fine, was smoothly applicable and compatible to the head hair without dripping. The applied foam gave substantially no irritating feeling to the scalp while being left on the head hair, and no dyeing unevenness. The whole hair was almost uniformly dyed.

The invention claimed is:

1. A two-part hair dye comprising a first part comprising an alkali agent, a second part comprising hydrogen peroxide, and a non-aerosol foamer vessel to discharge in the form of foam a liquid mixture of the first part and the second part, wherein at least one of the first part and the second part comprises a surfactant, 90% by mass or more of the total amount of which being a nonionic surfactant component.

2. The two-part hair dye according to claim 1, wherein the liquid mixture of the first part and the second part further comprises a higher alcohol.

3. A method for dyeing hair, comprising the steps of discharging in the form of foam the liquid mixture in the two-part hair dye according to claim 1 or 2 from a non-aerosol foamer vessel; applying the foam to the head hair; and re-foaming the foam on the head hair.

* * * * *